United States Patent [19]

Ornstein

[11] Patent Number: 4,968,678

[45] Date of Patent: Nov. 6, 1990

[54] TETRAZOLE EXCITATORY AMINO ACID RECEPTOR ANTAGONISTS

[75] Inventor: Paul L. Ornstein, Indianapolis, Ind.

[73] Assignee: Eli Lilly and Company, Indianapolis, Ind.

[21] Appl. No.: 371,568

[22] Filed: Jun. 26, 1989

Related U.S. Application Data

[63] Continuation-in-part of Ser. No. 278,651, Dec. 5, 1988, abandoned, which is a continuation-in-part of Ser. No. 157,760, Feb. 19, 1988, abandoned.

[51] Int. Cl.$^5$ .................. A61K 31/445; A61K 31/41; C07D 401/06
[52] U.S. Cl. .............................. 514/222.2; 514/222.5; 514/222.8; 546/210
[58] Field of Search ...................... 546/210; 514/222.2, 514/222.5, 222.8

[56] References Cited

U.S. PATENT DOCUMENTS 3,536,715 10/1970 Hayao et al. ...................... 546/210
4,746,653 5/1988 Hutchinson et al. ................ 514/89

FOREIGN PATENT DOCUMENTS

A81455/87 5/1988 Australia ............................ 546/23
159889 10/1985 European Pat. Off. ............ 514/255
203891 12/1986 European Pat. Off. ............. 546/22

OTHER PUBLICATIONS

Jacobson et al., *Neuroscience* 19, 267–273, (1986).
Collins, *Brain Research*, 244, 311–318 (1982).

*Primary Examiner*—Robert T. Bond
*Attorney, Agent, or Firm*—Joseph A. Jones; Leroy Whitaker

[57] ABSTRACT

The present invention provides novel tetrazole derivatives useful as excitatory amino acid receptor antagonists and in treating a variety of associated nervous system disorders.

22 Claims, No Drawings

TETRAZOLE EXCITATORY AMINO ACID RECEPTOR ANTAGONISTS

CROSS-REFERENCE

This application is a continuation-in-part of copending application 07/278,651, filed Dec. 5, 1988, now abandoned, which is a continuation-in-part of copending application Ser. No. 07/157,760, filed Feb. 19, 1988, now abandoned.

SUMMARY OF THE INVENTION

The present invention provides novel tetrazole derivatives which are antagonists of excitatory amino acid receptors. More specifically, the present invention relates to a compound of the formula

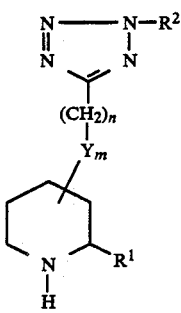

wherein:
the compound is in the (—) form;
$R^1$ is

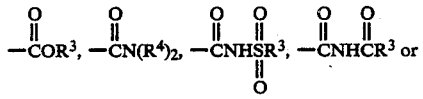

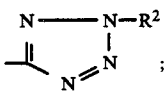

$R^2$ is hydrogen or $C_1$-$C_3$ alkyl;
n is 0, 1, 2 or 3;
m is 0 or 1;
provided that the sum of m and n is 0, 1, 2 or 3;
$R^3$ is hydrogen, $C_1$-$C_4$ alkyl, phenyl or an oral ester forming group;
Y is —CH=;
each $R^4$ independently is hydrogen, $C_1$-$C_4$ alkyl or phenyl; or
a pharmaceutically acceptable salt thereof.

The invention also provides pharmaceutical formulations comprising a compound of Formula I and a pharmaceutically acceptable carrier, diluent or excipient therefor.

Further embodiments of the invention include a method of blocking one or more excitatory amino acid receptors, as well as methods for treating a variety of disorders which have been linked to the excitatory amino acid receptors including neurological disorders (for example, epilepsy), stroke, anxiety, cerebral ischaemia, muscular spasms and neurodegenerative disorders such as Alzheimer's Disease and Huntington's Disease, employing a compound of Formula I.

DETAILED DESCRIPTION OF THE INVENTION

In the above formula, the terms "$C_1$-$C_3$ alkyl" and "$C_1$-$C_4$ alkyl" represent a straight or branched alkyl chain having from one to four carbon atoms, including methyl, ethyl, n-propyl, isopropyl, n-butyl, isobutyl, sec-butyl, and t-butyl.

The term "oral ester forming group," as used herein, represents a substituent which, when attached to the carboxylic acid group, forms an ester function suitable for administration to mammals in need of treatment. Examples of such oral ester forming groups include $C_1$-$C_4$ alkyl; benzyl; benzyl substituted on the phenyl ring with halogen, $C_1$-$C_4$ alkyl or $C_1$-$C_4$ alkoxy; $C_1$-$C_5$ alkanoyloxymethyl; or $C_1$-$C_5$ alkanoyloxymethyl substituted on the oxomethyl with $C_1$-$C_4$ alkyl or $C_4$-$C_7$ cycloalkyl.

While all the compounds of the present invention are believed to be antagonists of excitatory amino acid receptors, there are certain compounds of the invention which are preferred for such use. Preferably, $R^1$ is

and $R^2$ and $R^3$ are hydrogen. Another preferred group includes compounds wherein Y is —CH=. Still another preferred group includes salts of such compounds. Preferred compounds are also in the group wherein n is 0 or 1. Other preferred aspects of the present invention will be noted hereinafter.

The compounds of the present invention possess two asymmetric carbon atoms represented by the carbon atom of the piperidine ring which attaches to the tetrazole ring either directly or through one or more methylene groups, and the carbon atom of the piperidine ring which attaches $R^1$ to the piperidine ring. As such, the compounds can exist as two diastereoisomers, their cis or trans isomers, and each of which can exist as the racemic mixture of such isomers or each individual optical isomer. The compounds of the present invention include not only the (±)-racemates, but also their respective optically active (—)-isomers. When a Y group is present, it creates a third point of asymmetry, and the compounds accordingly include the E and Z isomers and the corresponding racemate. The cis isomers are preferred; and the cis-(—) isomers are particularly preferred.

When a compound of the invention is named without a stereochemical indication, the racemate and also the diastereomers and the stereospecific isomers are intended to be included. When a specific isomer or diastereomer is intended, it will be specifically named.

As pointed out above, this invention includes the pharmaceutically acceptable salts of the compounds defined by Formula I. These salts can exist in conjunction with the acidic or basic portion of the molecule and can exist as acid addition, primary, secondary, tertiary or quaternary ammonium or alkali metal or alkali earth metal salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, metaphosphate, pyrophosphate, chloride, lithium, bromide, iodide, acetate, magnesium, propionate, tetramethylammonium, decanoate, caprylate, acrylate, formate, isobutyrate, caprate, heptanoate, potassium, propiolate, oxalate, trimethylammonium, malonate, succinate, suberate, sebacate, fumarate., maleate, butyne-1,4-dioate, sodium, hexyne-1,6-dioate, benzoate, chlorobenzoate, methylbenzoate, dinitrobenzoate, hydroxybenzoate, methoxybenzoate, phthalate, sulfonate, methylammonium, xylenesulfonate, phenylacetate, phenylpropionate, phenylbutyrate, citrate, lactate, calcium, β-hydroxybutyrate, glycollate, maleate, tartrate, methanesulfonate, propanesulfonate, naphthalene-1-sulfonate, naphthalene-2-sulfonate, mandelate and the like salts.

It will be understood that salts of the individual stereospecific isomers or the diastereomers may be formed just as salts of the racemic mixture are prepared.

Compounds of the present invention will contain one or two tetrazole rings. Tetrazole is known to exist as tautomeric structures. The tetrazole having the double bond on the nitrogen atom at the 1-position and the $R^2$ substituent on the N-2 nitrogen atom is properly named as a 2H-tetrazole and is represented by the following structure:

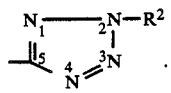

This compound has a corresponding tautomeric form wherein the $R^2$ substituent is at N-1 with the double bond on the nitrogen atom of the 4-position. These compounds are named in part as 1H-tetrazoles and possess the following part structure:

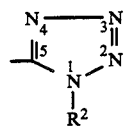

Mixtures of the two tautomers are referred to herein as 1(2)H-tetrazoles. The present invention contemplates both individual tautomeric forms as well as the combination of the two tautomers.

The compounds of the present invention may be prepared by procedures well known to those of ordinary skill in the art. Preferably, a hydroxy or hydroxyalkyl substituted 2-carbalkoxypyridine is reduced to the corresponding hydroxy or hydroxyalkyl substituted 2-carbalkoxypiperidine, which is blocked at the ring nitrogen with a standard blocking reagent. The blocked hydroxy or hydroxyalkyl substituted 2-carbalkoxypiperidine is converted to the halo or haloalkyl substituted 2-carbalkoxypiperidine, which is then converted to the corresponding cyano intermediate. When n is not zero, the blocked hydroxy substituted 2-carbalkoxypyridine is oxidized to the ketone, which is then converted to an α, β-unsaturated nitrile, and then to the desired cyano intermediate by hydrogenation. The cyano intermediate is converted to the blocked tetrazole substituted 2-carbalkoxypiperidine which is hydrolyzed to the compound of the present invention. This synthesis may be represented by the following scheme:

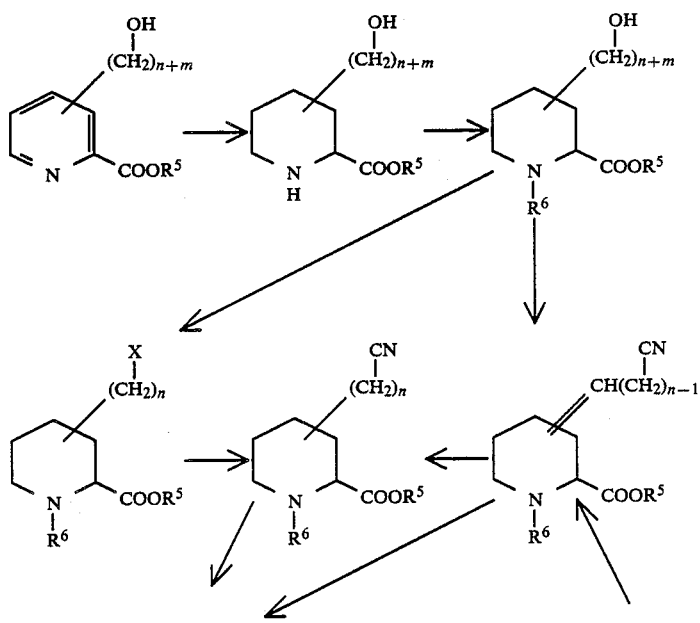

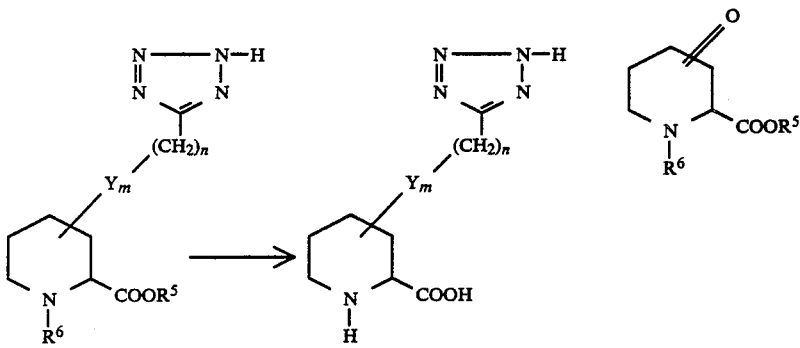

wherein n and m are as defined above, $R^5$ is $C_1$-$C_4$ alkyl, $R^6$ is a blocking group, preferably $C_1$-$C_6$ alkoxycarbonyl, allyl or vinyloxycarbonyl, and X is chloro, bromo or iodo.

The hydroxy or hydroxyalkyl substituted 2-carbalkoxypyridine is converted to the corresponding piperidine derivative according to standard reduction conditions. The starting pyridine is preferably converted to the hydrochloride salt. Preferably, the starting material is hydrogenated in the presence of a catalyst such as platinum oxide or rhodium on alumina and a suitable solvent. Suitable solvents include the alcohols, such as ethanol and especially methanol. The reaction is substantially complete after about one to about 24 hours when conducted at a temperature in the range of about 20° C. to about 100° C. The desired product is easily isolated by filtering the reaction mixture through infusorial earth and concentrating the filtrate under vacuum. The resulting residue may be further purified, if desired, but is preferably used directly in the following reaction.

The hydroxy or hydroxyalkyl substituted 2-carbalkoxypiperidine thus prepared is next blocked at the ring nitrogen atom with a standard blocking group to provide the corresponding blocked hydroxy or hydroxyalkyl substituted 2-carbalkoxypiperidine. This procedure is carried out by combining approximately equimolar quantities of the piperidine derivative with an equimolar or slight excess of a standard blocking reagent having a good leaving group such as methyl chloroformate or methyl bromoformate, or di-t-butyldicarbonate or the like, in the presence of a base. Typical bases include hydrides such as sodium hydride and tertiary amine bases such as Hunig's base. The reaction is conducted at a temperature in the range of about −20° C. to about 25° C. for a period of about 10 minutes to about 12 hours. The desired compound is isolated by extracting the desired compound into a water-immiscible organic solvent and concentrating the resulting solution, typically under vacuum. The residue is then generally further purified by standard techniques such as crystallization from common solvents or chromatographic purification over solid supports such as silica gel or alumina.

The blocked hydroxy or hydroxyalkyl substituted 2-carbalkoxypiperidine is next converted to the corresponding chloro, bromo or iodo substituted derivative by reaction with a standard halogenating agent in the presence of a tertiary amine base. Typical halogenating agents include triphenylphosphinedibromide, triphenylphosphinediiodide, triphenylphosphinedichloride and the like. The reaction is conducted at a temperature in the range of about −10° C. to about 25° C. for about 1 to about 12 hours and the product isolated by standard procedures.

The halo or haloalkyl substituted 2-carbalkoxypiperidine is next treated with a cyanating agent to afford the corresponding cyano or cyanoalkyl substituted 2-carbalkoxypiperidine. Typical cyanating agents suitable for use in this reaction include the alkali metal cyanides, especially sodium cyanide. The reaction is conducted by combining the brominated starting material with an equimolar to preferably an excess amount of the cyanating agent. The reaction is conducted at a temperature in the range of about 40° C. to about 150° C. for about 1 hour to about 120 hours and the product isolated and purified, if desired, by standard procedures.

The cyano derivative thus prepared is next converted to the tetrazole intermediate and then to the compound of the invention according to the following process. The cyano starting material is reacted with tributyltin azide (also known as azido tributylstannane). This reaction is conducted at a temperature of about 50° C. to about 120° C., preferably at about 80° C., for about 12 to about 120 hours. The product may be isolated, but is preferably hydrolyzed directly to a compound of the invention by standard acid or base hydrolysis. The reaction is conducted at a temperature in the range of about 50° C. to about 150° C. for about 2 hours to about 24 hours and the product isolated. The product may then be purified by standard procedures such as crystallization with common solvents such as water, acetone or ethanol, or chromatography over solid supports such as silica gel, ion exchange resins or standard absorbents.

Compounds of the invention wherein $R^1$ is other than the free carboxylic acid substituent are prepared by procedures well known to one of ordinary skill in the art. Compounds wherein $R^1$ is —C(=O)OR$^3$ and R$^3$ is $C_1$-$C_4$ alkyl are prepared by esterification of the free carboxylic acid with an appropriate alcohol $R^3$OH in the presence of hydrogen chloride gas. The compounds wherein $R^1$ is —C(=O)OR$^3$ and $R^3$ is an oral ester forming group are prepared by standard alkylation or acylation techniques. Compounds wherein $R^1$ is —C(=O)O-(phenyl), —C(=O)N(R$^4$)$_2$, —C(=O)NHSO$_2$R$^3$ or —C(=O)NHC(=O)R$^3$ are prepared by the reaction of the free carboxylic acid derivative of the piperidine intermediate, which is blocked at the 1-position of the piperidine ring with $R^6$ as defined above, with an appropriately substituted phenol $R^3$OH, amine NH(R$^4$)$_2$, sulfonamine NH$_2$SO$_2$R$_3$ or acylamine NH$_2$C(=O)R$^3$ in the presence of a coupling reagent and mutual organic solvent. Suitable coupling reagents include the carbodiimides such as N,N'-dicyclohexylcarbodiimide, N,N'-diisopropylcarbodiimide, or N,N'-diethylcarbodiimide;

the imidazoles such as carbonyldiimidazole; as well as reagents such as N-ethoxy-carbonyl-2-ethoxy-1,2-dihydroquinoline (EEDQ). The resulting compound is then deblocked at the 1-position as hereinbefore described. Compounds wherein $R^1$ is tetrazole or substituted tetrazole are prepared by hydrolyzing the cyano intermediate prepared as described above to the corresponding 2-carboxy derivative which is then treated with ammonia in the presence of a coupling reagent as described above to provide the corresponding primary carboxamide. The carboxamide is dehydrated to the corresponding carbonitrile upon treatment with phenylphosphinoyl dichloride or triphenylphosphine dibromide, both in the presence of a tertiary amine such as triethylamine or pyridine. The resulting compound is converted to the ditetrazole intermediate with at least two equivalents of tributyltin azide according to conditions hereinbefore described. The desired compound is then prepared as hereinbefore described.

Compounds of the present invention wherein the $R^2$ substituent on the tetrazole ring is other than hydrogen may also be prepared by known processes, or by processes analogous to such known procedures. Typically, alkylation of the unsubstituted starting material with an appropriate halide reagent provides the desired compound of the invention or an intermediate which can be further modified to a compound of the invention as herein described. If a base is employed in the alkylation reaction, addition occurs first on the tetrazole ring if the other free nitrogen atoms are unsubstituted. Any free nitrogen atom may also be blocked prior to the reaction, and deblocked subsequently according to standard conditions employing standard blocking reagents. Of course, disubstitution with the same substituent merely requires the use of an appropriate molar excess of reagent to account for each of the desired substituents on the final compound.

When the product is a compound wherein a Y group is present, the process can begin with an oxy-substituted 2-carbalkoxy blocked piperidine, which is cyanated with diethyl cyanoalkylphosphonate or cyanoalkyltriphenylphosphonium halide, to prepare the desired cyanoalkylidene intermediate. The cyano group of it may be converted to the tetrazole, as described above, leaving the alkylidene linkage intact. Alternatively, the general process may be used by omitting the usual reduction of the cyanoalkylidene intermediate.

The preceding description of the synthesis of the compounds of the present invention prepares a mixture of the cis- and trans-isomers, but predominantly as the cis-isomer. The diastereomers are easily separated from the mixture using standard chromatographic techniques, for example, employing silica gel or alumina adsorbents. An isolated diastereomer may be converted to the other diastereomer by treatment with a base such as a tertiary amine base or an alkali metal alkoxide in the corresponding alcohol. While separation or conversion may be conducted on any piperidine derivative in the foregoing synthetic scheme, preferably such separation or conversion is carried out on the blocked hydroxy or hydroxyalkyl substituted 2-carbalkoxypiperidine as defined above.

Further, the (−) isomers of the compounds may be separated by forming a salt of the compounds in the carboxylate form with an optically active salt, such as a D-tartrate, and separating the isomers by differential crystallization or other conventional separation means. It is preferred to carry out such a separation on an intermediate wherein the group at the 4-position of the piperidine is cyano or cyanoalkyl, and the nitrogen is blocked with allyl or a like group. Alternatively, the separation of (−) isomers may be carried out on intermediates in the carboxylic acid form by preparing salts with optically active bases. The separation of isomers is further illustrated by Examples 8-9 below.

The pharmaceutically acceptable salts of the invention are typically formed by reacting a piperidinetetrazole of the invention with an equimolar or excess amount of salt forming reagent. The reactants are generally combined in a mutual solvent such as diethyl ether, benzene, ethanol or water and the salt normally precipitates out of solution within about one hour to 10 days, and can be isolated by filtration.

The hydroxy or hydroxyalkyl substituted 2-carbalkoxypyridines employed as starting materials in the synthesis of the compounds of this invention are known and easily prepared by procedures well known to those of ordinary skill in the art. For example, a pyridyl($C_1$-$C_4$)alkanoic acid ester is converted to the corresponding hydroxy substituted pyridine, which is acylated and converted to the N-oxide derivative. The acylated(N-oxide)pyridine is converted to a 2-cyano(acylated)pyridine which is finally converted to a hydroxy or hydroxyalkyl substituted 2-carbalkoxypyridine. This reaction may be represented by the following scheme:

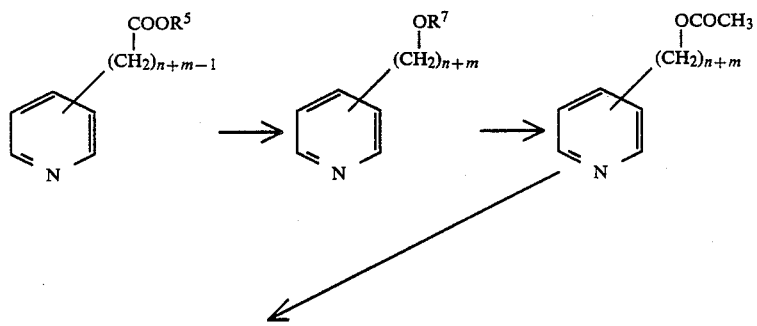

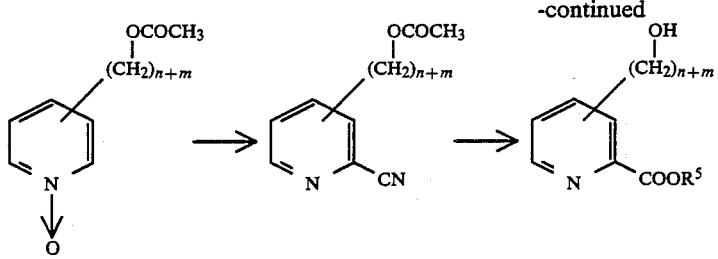

wherein n and m are as defined above, $R^5$ is $C_1$-$C_4$ alkyl and $R^7$ is hydrogen or methyl.

The following Examples further illustrate the compounds of the present invention and methods for their synthesis. The Examples are not intended to be limiting to the scope of the invention in any respect and should not be so construed.

EXAMPLE 1 cis-($\pm$)-4-[2-(1(2)H-Tetrazol-5-yl)ethyl]-2-piperidinecarboxylic acid

A. 4-Pyridineethanol

Fifteen grams (0.091 mol) of 4-pyridineacetic acid ethyl ester was dissolved in 180 ml of dry THF. The solution was transferred to a 1 l., 3-neck round bottom flask which had been flushed with nitrogen. To the mixture was added dropwise 55 ml of 1.0 M lithium aluminum hydride (0.055 mol) at approximately 0° C. The reaction mixture became yellow upon addition of the reducing agent. Following addition, the mixture was quenched with 2.1 ml of water at 0° C. followed by 2.1 ml of 15% by volume of sodium hydroxide and 6.3 ml of water. The mixture was allowed to stir at room temperature for approximately 4 hours and filtered through Celite. The filtrate was concentrated under vacuum to provide 6.38 g of 4-pyridineethanol. This material was used directly in the following reaction.

B. 4-Pyridineethanol acetate

To a solution of 11.3 ml of acetic anhydride in 100 ml of methylene chloride was added approximately 125 mg of dimethylaminopyridine, and the solution was cooled to 0° C. In a separate container 12.2 g (0.099 mol) of 4-pyridineethanol was suspended in 80 ml of methylene chloride and 12.14 g (0.120 mol, 16.7 ml) of triethylamine was added. This mixture was added to the acetic anhydride solution slowly by pipet. The resulting mixture was stirred at room temperature for approximately 90 minutes and quenched with about 100 ml of water. The mixture was placed in a separatory funnel and the organic layer was isolated and washed two times with 100 ml portions of water. The aqueous layers were combined and extracted two times with methylene chloride and one time with diethyl ether. The organic extracts were combined, dried over anhydrous sodium sulfate, filtered and concentrated under vacuum to provide 16.2 g of the desired compound. Purification by high pressure liquid chromatography provided 11.19 g of 4-pyridineethanol acetate.

C. 4-Pyridineethanol acetate 1-oxide

To a solution of 38.82 g (0.18 mol, 80% by weight) of 3-chloroperoxybenzoic acid in 360 ml of acetone was added 24.70 g (0.15 mol) of 4-pyridineethanol acetate neat via pipet (20 ml acetone rinse). The reaction mixture was allowed to stir for approximately one hour at room temperature until all of the starting material had been consumed as indicated by thin layer chromatography in ethanol:ethyl acetate (1:9, v:v). The reaction mixture was concentrated under vacuum and the residue was partitioned between 300 ml of water and 300 ml of diethyl ether. The aqueous layer was separated, extracted three times with diethyl ether and the organic extracts were combined. The combined organic phases were washed three times with water. The organic layers were discarded and the combined aqueous layers were concentrated under vacuum. The resulting residue was dissolved in chloroform and the solution was dried over anhydrous magnesium sulfate and concentrated under vacuum. The residue was dried under vacuum to afford 24.06 g of 4-pyridineethanol acetate 1-oxide which was used directly in the following reaction.

D. 4-[2-(Acetyloxy)ethyl]-2-pyridinecarbonitrile

To a solution of 24.06 g (0.13 mol) of 4-pyridineethanol acetate 1-oxide dissolved in 260 ml of methylene chloride was added 15.87 g (0.16 mol, 21.4 ml) of trimethylsilylcyanide. The mixture was stirred for approximately 5 minutes and 17.21 g (0.16 mol, 16.6 ml) of N,N-dimethylcarbamoyl chloride was added. The reaction was mildly exothermic. The mixture was stirred at room temperature overnight and 440 ml of 10% by weight aqueous potassium carbonate was added carefully. The mixture was stirred for approximately 15 minutes and the organic layer was separated. The aqueous layer was extracted three times with methylene chloride and the organic extracts were combined, dried over anhydrous sodium sulfate and concentrated under vacuum to afford 25.5 g of the desired compound. This material was chromatographed by high pressure liquid chromatography to provide 18.45 g of 4-[2-(acetyloxy)ethyl]-2-pyridinecarbonitrile as an off-white solid mp =49°-52° C.

E. Methyl 4-(2-hydroxyethyl)-2-pyridinecarboxylate

A 1 l. round bottom flask was charged with 18.24 g (0.096 mol) of 4-[2-(acetyloxy)ethyl]-2-pyridinecarbonitrile and 380 ml of methanol. To the reaction mixture was added 96 ml of 5N aqueous potassium hydroxide and the reaction mixture was refluxed overnight with stirring. The reaction mixture was cooled and concentrated under vacuum. To the residue was added methanol saturated with hydrochloric acid (400 ml), and the resulting mixture was heated to reflux for 30 minutes, cooled and concentrated under vacuum. To the residue was added 400 ml of methanol saturated with hydrochloric acid. The mixture was refluxed overnight, cooled to room temperature and concentrated under vacuum. The mixture was partitioned between methylene chloride and 20% by weight potassium bicarbonate in water. The organic layer was separated, and the aqueous layer was extracted three times with methylene chloride and one time with diethyl ether. The organic extracts were combined, dried over anhydrous sodium sulfate, filtered and concentrated under vacuum to provide 11.51 g of the desired compound. The aqueous layer was concentrated to approximately half its original volume, extracted three times with methylene chloride and one time with diethyl ether. The organic extracts were combined, dried over anhydrous sodium sulfate and concentrated under vacuum as described above to provide an additional 1.15 g of the desired compound. The crude products were combined and purified by high pressure liquid chromatography to provide 9.02 g of methyl 4-(2-hydroxyethyl)-2-pyridinecarboxylate as a clear oil.

F. Methyl cis-4-(2-hydroxyethyl)-2-piperidinecarboxylate

Methyl 4-(2-hydroxyethyl)-2-pyridinecarboxylate (9.02 g, 0.050 mol) was placed in a 250 ml round bottom flask and 100 ml of methanol saturated with gaseous hydrochloric acid was added (pH 1). The resulting solution was concentrated under vacuum to afford 10.98 g of the hydrochloride salt. This material was hydrogenated at 50° C. and 60 p.s.i. overnight employing 89 ml of methanol and 1.8 g of platinum oxide. The mixture was filtered through Celite, washed with methanol and concentrated under vacuum to provide 10.64 g of methyl cis-4-(2-hydroxyethyl)-2-piperidinecarboxylate, used directly without purification.

G. Methyl cis-4-(2-hydroxyethyl)-N-t-butoxycarbonyl-2-piperidinecarboxylate

To a 500 ml round bottom flask was added 10.64 g (0.048 mol) of methyl cis-4-(2-hydroxyethyl)-2-piperidinecarboxylate and 160 ml of methylene chloride. To the mixture was added 18.10 g (0.14 mol, 24.4 ml) of Hunig's base and the resulting mixture was gently agitated until all the starting material was dissolved. The mixture was cooled to 0° C., 12.66 g (0.058 mol, 13.3 ml) of di-t-butyldicarbonate was added and the mixture was stirred overnight warming to room temperature. To the mixture was added 200 ml of methylene chloride, and the solution was washed three times with 100 ml portions of an aqueous solution of 10% by weight sodium bisulfate. The aqueous layers were combined and extracted twice with methylene chloride and once with diethyl ether. The organic extracts were combined and washed three times with a saturated sodium bicarbonate solution. The aqueous layers were combined and extracted twice with methylene chloride and once with diethyl ether. The organic extracts were combined, dried over anhydrous magnesium sulfate, filtered and concentrated under vacuum to provide 16.31 g of residue. High pressure liquid chromatography of the residue provided 11.58 g of methyl cis-4-(2-hydroxyethyl)-N-t-butoxycarbonyl-2-piperidinecarboxylate.

H. Methyl cis-4-(2-bromoethyl)-N-t-butoxy-carbonyl-2-piperidinecarboxylate

Dibromotriphenylphosphine was prepared by combining 9.00 g (0.035 mol) of triphenylphosphine and 5.50 g (1.80 ml, 0.035 mol) of bromine in 90 ml of methylene chloride at 0° C. To this mixture was added 9.00 g (0.031 mol) of methyl cis-4-(2-hydroxyethyl)-N-t-butoxycarbonyl-2-piperidinedicarboxylate and 3.70 g (3.8 ml, 0.047 mol) of pyridine in 10 ml of methylene chloride. The reaction mixture was stirred for one hour at 0° C. and diethyl ether was added. The reaction mixture was washed twice with an aqueous solution of 10% by weight sodium bisulfate, dried over anhydrous sodium sulfate, filtered and concentrated under vacuum. The resulting residue was suspended in diethyl ether, filtered and concentrated under vacuum. The residue was again suspended in diethyl ether and filtered, and the filtrate combined with the residue from the first filtration. The resulting mixture was concentrated under vacuum to provide 12.95 g of methyl cis-4-(2-bromoethyl)-N-t-butoxycarbonyl-2-piperidinecarboxylate as an oily solid, used without further purification in the next reaction.

I. Methyl cis-4-(2-cyanoethyl)-N-t-butoxycarbonyl-2-piperidinecarboxylate

To a solution of 12.95 g (0.031 mol, containing triphenylphosphine oxide) of methyl cis-4-(2-bromoethyl)-N-t-butoxycarbonyl-2-piperidinecarboxylate and 40 ml of DMSO was added 2.30 g (0.047 mol) of sodium cyanide. The mixture was stirred for approximately 30 minutes at 50° C. To the mixture was added 50 ml each of water and brine and the mixture was extracted four times with methylene chloride and once with diethyl ether. The organic extracts were combined, washed twice with water and once with brine, dried over anhydrous sodium sulfate and concentrated under vacuum. The resultant residue was dissolved in 100 ml of ethyl acetate:hexane (1:3, v:v) and filtered through a one inch pad of silica gel (230–400 mesh) in a 150 ml medium porosity sintered glass funnel. The silica gel pad was washed with an additional 400 ml of ethyl acetate:hexane (1:3, v:v). The filtrate was concentrated under vacuum to afford 7.85 g of methyl cis-4-(2-cyanoethyl)-N-t-butoxycarbonyl-2-piperidinecarboxylate.

J. A 250 ml round bottom flask was charged with 7.57 g (0.026 mol) of methyl cis-4-(2-cyanoethyl)- N-t-butoxycarbonyl-2-piperidinecarboxylate and 17.0 g (0.051 mol) of tributyltin azide. The resulting mixture was heated at 80° C for approximately 48 hours and cooled to room temperature. To the mixture was added 100 ml of methanol saturated with hydrochloric acid. The mixture was stirred two hours at room temperature and concentrated under vacuum. To the mixture was added 50 ml of 6N hydrochloric acid and 150 ml of diethyl ether. The aqueous layer was separated and extracted again with 150 ml of diethyl ether. The aqueous layer was concentrated under vacuum. The residue was dissolved in 50 ml of 6N hydrochloric acid. The resulting mixture was heated at reflux overnight, cooled and concentrated under vacuum. The residue was dissolved in water, treated with 4.2 g of propylene oxide at 50° C. for one hour, and concentrated under vacuum. The residue was dissolved in a minimum amount of water, and the resulting mixture was cooled to 0° C. for 72 hours. The precipitated crystals were collected by vacuum filtration and washed with water, acetone and diethyl ether. The crystals were recrystallized from water to provide 3.25 g of cis-($\pm$)-4-[2-(1(2)H-tetrazol-5-yl)ethyl]-2-piperindinecarboxylic acid dihydrate. mp = 260°–265° C.

Analysis calculated for $C_9H_{15}N_5O_2 \cdot 2H_2O$
Theory: C, 41.37; H, 7.33; N, 26.80;
Found: C, 41.60; H, 7.27; N, 26.75.

The compound of Example 2 was prepared according to the general procedure described in Example 1.

EXAMPLE 2 cis-(±)-4-[3-(1(2)H-Tetrazol-5-yl)propyl]-2-piperidinecarboxylic acid, mp =257°-261° C.

Analysis calculated for $C_{10}H_{17}N_5O_2$
Theory: C, 50.20; H, 7.16; N, 29.82;
Found: C, 49.90; H, 7.23; N, 29.52.

EXAMPLE 3 cis-(±)-4-[(1(2)H-Tetrazol-5-yl)methyl]-2-piperidinecarboxylic acid

A. 4-Hydroxy-2-pyridinecarboxylic acid hydrobromide

To a solution of 30.5 g (0.24 mol) of 4-methoxypyridine-N-oxide in 250 ml of methylene chloride was added 30.3 g (0.31 mol, 40.7 ml) of trimethylsilyl cyanide. Approximately five minutes later 32.8 g (0.31 mol, 28.0 ml) of N,N-dimethylcarbamoyl chloride was added in four 7 ml portions over one hour. The resulting mixture was stirred overnight at room temperature. To the mixture was carefully added 250 ml of 10% by weight aqueous potassium carbonate. After 15 minutes at room temperature the organic layer was separated and the aqueous layer was extracted twice with methylene chloride and once with diethyl ether. The combined organic extracts were dried over anhydrous magnesium sulfate, filtered and concentrated under vacuum. The residue was dissolved in 150 ml of 48% by weight aqueous hydrobromic acid. The resulting mixture was heated to reflux overnight and cooled to 0° C. The crystals that formed were collected by vacuum filtration, washed with diethyl ether, and dried under vacuum at 50° C. to afford 45.5 g of 4-hydroxy-2-pyridinecarboxylic acid hydrobromide.

B. Ethyl 4-hydroxy-2-pyridinecarboxylate hydrochloride

To a 1 l. round bottom flask was added 45.5 g (0.21 mol) of 4-hydroxy-2-pyridinecarboxylic acid hydrobromide and 500 ml of ethanol saturated with hydrochloric acid. The mixture was heated to reflux overnight, cooled and concentrated under vacuum to 1/3 of its original volume. After cooling the mixture to about 0° C., the resultant crystals were collected by vacuum filtration, washed with ethanol and diethyl ether, and dried under vacuum to afford 29.5 g of ethyl 4-hydroxy-2-pyridinecarboxylate hydrochloride.

C. Ethyl cis-4-hydroxy-N-t-butoxycarbonyl-2-piperidinecarboxylate

Ethyl 4-hydroxy-2-pyridinecarboxylate hydrochloride (27.2 g, 0.13 mol) was hydrogenated in 200 ml of ethanol with 15.5 g of 5% by weight rhodium on alumina at 100° C. and 1000 p.s.i. for 10 hours. The mixture was cooled, filtered and concentrated under vacuum. To the residue was added 250 ml of methylene chloride, 50 ml of ethanol and 25.2 g (0.20 mol, 34.0 ml) of Hunig's base, followed by the dropwise addition of 28.4 g (0.13 mol, 29.9 ml) of di-t-butyldicarbonate over a period of thirty minutes. After one hour the mixture was concentrated under vacuum, and the residue was dissolved in methylene chloride and washed twice with 10% by weight aqueous sodium bisulfate. The combined aqueous washes were extracted once with methylene chloride and once with diethyl ether. The organic extracts were combined, dried over anhydrous sodium sulfate, filtered and concentrated under vacuum. High pressure liquid chromatography of the residue provided 21.3 g of ethyl cis-4-hydroxy-N-t-butoxycarbonyl-2-piperidinecarboxylate as a colorless oil.

D. Ethyl 4-oxo-N-t-butoxycarbonyl-2-piperidinecarboxylate

To a 1 l. round bottom flask was added 33.6 g (0.16 mol) of pyridinium chlorochromate, 35 g of powdered 4A molecular sieves and 200 ml of methylene chloride. After stirring the mixture at room temperature for sixty minutes, a solution of 21.3 g (0.078 mol) of ethyl cis-4-hydroxy-N-t-butoxycarbonyl-2-piperidinecarboxylate in 50 ml of methylene chloride was added. After stirring the mixture for sixty minutes at room temperature, 700 ml of diethyl ether was added. The mixture was filtered through three-fourths inch of Celite and three-fourths inch of silica gel (230-400 mesh) in a 650 ml medium porosity sintered glass funnel. The solids were washed with 1 l. of diethyl ether and the filtrate was concentrated under vacuum. To the residue was added 200 ml of diethyl ether and the mixture filtered through three-eighths inch of Celite and three-eighths inch of silica gel (230-400 mesh) in a 150 ml medium porosity sintered glass funnel. The solids were washed with 500 ml of diethyl ether and the filtrate was concentrated under vacuum. The residue was purified by high pressure liquid chromatography to provide 14.6 g of ethyl 4-oxo-N-t-butoxycarbonyl-2-piperidinecarboxylate as a colorless oil.

E. Ethyl 4-cyanomethylidene-N-t-butoxycarbonyl-2-piperidinecarboxylate

To a suspension of 0.75 g (0.019 mol, 60% by weight in oil) of sodium hydride (washed three times with hexanes) in 40 ml of THF was added 3.34 g (0.019 mol) of diethylcyanomethylphosphonate. After stirring the reaction mixture for thirty minutes at room temperature, a solution of 4.26 g (0.016 mol) of ethyl 4-oxo-N-t-butoxycarbonyl-2-piperidinecarboxylate in 10 ml of THF was added. The mixture was stirred for 30 minutes at room temperature and 90 minutes at the reflux temperature of the reaction mixture, then cooled to room temperature and quenched with water. The organic layer was separated and the aqueous layer extracted twice with diethyl ether. The organic extracts were combined, dried over anhydrous magnesium sulfate, filtered and concentrated under vacuum. High pressure liquid chromatography of the residue afforded 3.58 g of ethyl 4-cyanomethylidene-N-t-butoxycarbonyl-2-piperidinecarboxylate.

F. Ethyl cis-4-cyanomethyl-N-t-butoxycarbonyl-2-piperidinecarboxylate

Ethyl 4-cyanomethylidene-N-t-butoxycarbonyl-2-piperidinecarboxylate (9.00 g, 0.031 mol) was hydrogenated in 140 ml of ethanol with 0.90 g of 5% by weight palladium-on-carbon at room temperature and 60 p.s.i. for 60 minutes. The mixture was filtered through Celite and concentrated under vacuum. High pressure liquid chromatography of the residue provided 8.20 g of ethyl cis-4-cyanomethyl-N-t-butoxycarbonyl-2-piperidinecarboxylate.

G. Ethyl cis-4-cyanomethyl-N-t-butoxycarbonyl-2-piperidinecarboxylate (8.0 g, 27.0 mmol) and 17.9 g (54.0 mmol) tributyltin azide were heated to 80° C. for 72 hours. The mixture was cooled to room temperature and charged with 10 ml of methanol. To this solution was added 100 ml of methanol saturated with hydrochloric gas. After stirring for two hours at room temperature, the mixture was concentrated under vacuum and partitioned between 6N aqueous hydrochloric acid and diethyl ether. The layers were separated and the aqueous layer extracted again with diethyl ether. The aqueous layer was concentrated under vacuum. The residue was dissolved in 70 ml of 6N aqueous hydrochloric acid. The mixture was heated to reflux overnight, cooled to room temperature and concentrated under vacuum. The residue was dissolved in water, treated with 6 ml of propylene oxide at 50° C. for one hour, and concentrated under vacuum. To the residue was added 75 ml of ethanol, and the resulting mixture was heated at reflux for one hour. The mixture was cooled, and the resultant precipitate was collected by vacuum filtration and washed with ethanol and acetone. The precipitate was suspended in acetone and refluxed for one hour. The mixture was cooled and filtered. The precipitate was washed with acetone and diethyl ether, and dried under vacuum to afford 3.0 g of cis-(±)-4-[(1(2)H-tetrazol-5-yl)methyl]-2-piperidinecarboxylic acid acetone solvate. mp =0 125°–128° C.

Analysis calculated for $C_8H_{13}N_5O_2 \cdot C_3H_6O$
Theory: C, 46.68; H, 7.44; N, 27.22;
Found: C, 46.58; H, 7.12; N, 27.28.

EXAMPLE 4

Z-(±)-4-[(1(2)H-Tetrazol-5-yl)methylidene]-2-piperidinecarboxylic acid

A 2.16 g portion of ethyl 4-cyanomethylidene-N-methoxycarbonyl-2-piperidinecarboxylate (prepared according to steps A-E of Example 3 above) was dissolved in 5 ml of 1,2-dimethoxyethane, and 5.69 g of tributyltin azide was added. The mixture was stirred at 80° C. for six days. A total of 6 g of additional azide was added from time to time during the reaction. The mixture was cooled at the end of the reaction period, and 50 ml of diethyl ether was added. Hydrogen chloride gas was bubbled through the solution for about five minutes, until it became cloudy, and the mixture was then concentrated under vacuum. Fifty ml of acetonitrile was added, and the mixture was extracted five times with a total of 500 ml of hexane. The hexane extracts were discarded, and the acetonitrile layer was concentrated under vacuum. The residue was chromatographed on 100 g of silica gel, eluting with 4% acetic acid in diethyl ether. The product-containing fractions were combined and concentrated under vacuum to obtain 1.7 g of crude product, which was heated under reflux with 70 ml of 6N hydrochloric acid for 20 hours. The mixture was then cooled and concentrated under vacuum to obtain a solid product. Water was added, and the solid was filtered and washed with acetone and ether and dried under vacuum to afford 0.42 g of product as the dihydrate.

Analysis calculated for $C_8H_1N_5O_2 \cdot 2H_2O$
Theory: C, 39.18; H, 6.17; N, 28.56;
Found: C, 39.17; H, 6.01; N, 28.31.

EXAMPLE 5

Butyl cis-(±)-4-[(1(2)H-tetrazol-5-yl)methyl]-2-piperidinecarboxylate

A 1.02 g portion of the product of Example 3 was esterified by adding it to 250 ml of n-butanol, saturated with hydrogen chloride. The mixture was heated under reflux overnight, and was then cooled and concentrated under vacuum. The residue was dissolved in water, and was purified by eluting it through an ion exchange column with 10% pyridine in water. The product-containing fractions were combined and concentrated under vacuum, and the residue was suspended in acetone and heated under reflux for one hour. That mixture was then filtered, and the filtrate was concentrated under vacuum. The residue was taken up in diethyl ether, and that mixture was filtered. The solids were washed with diethyl ether, to obtain 0.50 g of the desired product. mp =182°–185° C.

Analysis calculated for $C_{12}H_{21}N_5O_2$
Theory: C, 53.92; H, 7.92; N, 26.20;
Found: C, 53.66; H, 8.02; N, 26.05.

EXAMPLE 6

Ethyl cis-(±)-4-[(1(2)H-tetrazol-5-yl)methyl]-2-piperidinecarboxylate

A 1.05 g portion of the product of Example 3 was esterified in ethanol, sustantially as described in Example 5 above, except that the solid obtained after ion exchange was unsoluble in acetone and so it was filtered, washing with acetone and diethyl ether to obtain 0.75 g of the desired product, mp =98°–101° C.

Analysis calculated for $C_{10}H_{17}N_5O_2 \cdot 0.95H_2O$
Theory: C, 46.84; H, 7.43; N, 27.31;
Found: C, 46.49; H, 7.11; N, 27.91.

EXAMPLE 7 cis-(±)-4-[(1(2)-Methyl-1(2)H-tetrazol-5-yl)methyl]-2-piperidinecarboxylic acid

Four g of ethyl cis-(±)-4-[(1(2)H-tetrazol-5-yl)methyl]-N-methoxycarbonyl-2-piperidinecarboxylate was added to 0.6 g of sodium hydride in 16 ml of dimethyl formamide. The solution was stirred under nitrogen for one hour, and then 1.9 g of methyl iodide was added in 1 ml of dimethyl formamide. The mixture was stirred overnight at ambient temperature, and then 0.06 g of additional hydride was added and the mixture was stirred for three hours more. About 2 ml of water was added slowly to quench the hydride, and then the mixture was concentrated under vacuum. The residue was taken up with ethyl acetate and water, and the organic layer was dried over magnesium sulfate and concentrated under vacuum to obtain 3.2 g of residue. The crude product was purified by chromatography over 250 g of silica gel, eluting with 7:3 isopropanol:acetic acid. The product-containing fractions were concentrated under vacuum to obtain 1.47 g of product, in the blocked form.

A 1.39 g portion of the above intermediate was added to 50 ml of 6N hydrochloric acid, and the mixture was heated under reflux overnight and cooled. It was then concentrated under vacuum, and the residue was purified on an ion exchange column, eluting with 10% pyridine in water. The product-containing fractions were combined and concentrated under vacuum, and the residue was heated under reflux in acetone for one hour. The mixture was then cooled and filtered, and the residue was oven-dried to obtain 0.184 g of the desired product, in hydrate form.

Analysis calculated for $C_9H_{15}N_5O_2 \cdot 1.3H_2O$
Theory: C, 43.47; H, 7.13; N, 28.16;
Found: C, 43.78; H, 6.71; N, 27.82.

EXAMPLE 8 cis-(-)-4-(1(2)H-Tetrazol-5-yl)methyl]-2-piperidinecarboxylic acid

A Ethyl cis-(±)-4-cyanomethyl-N-allyl-2-piperidinecarboxylate

To a solution of 19.9 g (67.2 mmol) of ethyl 4-cyanomethyl-N-t-butoxycarbonyl-2-piperidinecarboxylate (prepared in Example 3F) in 100 ml of dichloromethane was added 50 ml of trifluoroacetic acid ($CO_2$ evolution). The mixture was stirred for 3 hr at room temperature and then was concentrated under vacuum. To the residue was added 100 ml of dichloromethane, and the solution was again concentrated under vacuum. The residue was dissolved in 200 ml of dichloromethane, 200 ml of saturated aqueous sodium bicarbonate was added, and the mixture was stirred for 15 minutes at room temperature. The organic layer was separated and washed with 100 ml of saturated aqueous sodium bicarbonate, and the combined aqueous washes were extracted twice with 100 ml each of dichloromethane and once with 50 ml of diethyl ether. The combined organic extracts were dried over $Na_2SO_4$, filtered and concentrated to afford 12.7 g (96%) of ethyl 4-cyanomethyl-2-piperidinecarboxylate. GC analysis showed an 85:15 mixture of cis:trans isomers. To a solution of 11.6 g (59.1 mmol) of the product in 60 ml of dimethylsulfoxide was added 9.9 g (118.2 mmol) of sodium bicarbonate and 5.7 ml (7.9 g, 65.0 mmol) of allyl bromide. After 1 hr at room temperature, another 1.1 ml portion of allyl bromide was added, and after another 2 hours at room temperature, the mixture was poured into 100 ml of water and 100 ml of brine and was extracted 5 times with 50 ml each of dichloromethane and once with 50 ml of diethyl ether. The combined organics were washed with 100 ml of water, then dried over $Na_2SO_4$, filtered and concentrated. The residue was purified by preparative HPLC to afford 8.6 g (62%) of ethyl cis-(±)-4-cyanomethyl-N-allyl-2-piperidinecarboxylate and 1.2 g (9%) of ethyl trans-(±)-4-cyanomethyl-N-allyl-2-piperidinecarboxylate, both of which were >99.9% one isomer by GC.

B. Ethyl cis-(+)-4-cyanomethyl-N-allyl-2-piperidinecarboxylate di-p-toluoyl-D-and L-tartrate salt A mixture of 7.36 g (31.1 mmol) of the racemic product above, 12.0 g (31.1 mmol) of di-p-toluoyl-D-tartrate and 0.56 ml (0.56 g, 31.1 mmol) of water were dissolved in ethyl acetate with heating. The solution was filtered and most of the ethyl acetate was removed to give a final volume of about 50 ml. The mixture was cooled to room temperature, and the crystals that formed were collected and washed with ethyl acetate, diethyl ether and pentane and dried to afford 13.0 g (67%). The material was recrystallized from ethyl acetate to afford 6.4 g (33%) of the desired (+)-salt, m.p. 142–142.2° C., $[\alpha]_D = +108.9°$ (c=1, methanol). A small portion of the (+)-salt was free based, and $^1H$ NMR of it in de-benzene with one equivalent of R-(−)-2,2,2-trifluoro-1-(9-anthryl)ethanol showed it to be <97% one enantiomer.

C. Ethyl cis-(+)-4-cyanomethyl-N-allyl-2-piperidinecarboxylate

To a flask were added 6.0 g (9.7 mmol) of the (+)-salt prepared above, 100 ml of dichloromethane and 100 ml of saturated aqueous sodium bicarbonate. The mixture was stirred for 10 min at room temperature, the organic layer was separated, and the aqueous layer was extracted thrice with 100 ml each of dichloromethane and once with 75 ml of diethyl ether. The combined organic extracts were dried over $Na_2SO_4$, filtered and concentrated. The residue was purified on 100 g of silica gel, eluting with 1/1 ethyl acetate/hexane to afford 2.0 g (89%) of ethyl cis-(+)-4-cyanomethyl-N-allyl-2-piperidinecarboxylate, $[\alpha]_D = +72.3°$ (C=1, dichloromethane).

D. Ethyl cis-(-)-4-cyanomethyl-N-vinyloxycarbonyl-2-piperidinecarboxylate

A solution of 2.0 g of the product from step C above, 1.8 g (16.5 mmol) of vinyl chloroformate and 3.5 g (16.5 mmol) of 1,8-bis-dimethylaminonaphthalene in 40 ml of dichloromethane was heated to reflux for 6 hr. The mixture was then cooled to ambient temperature and concentrated under vacuum. The residue was dissolved in diethyl ether and was washed twice with 10% aqueous sodium hydrogen sulfate and once with saturated aqueous sodium bicarbonate. The organic layer was dried over magnesium sulfate, filtered and concentrated under vacuum. Preparative HPLC afforded 1.8 g (79%) of the desired intermediate, $[\alpha]_D = -24.8°$ (c=1, dichloromethane).

E. cis-(-)-4-[(1(2)H-Tetrazol-5-yl)methyl]-2-piperidinecarboxylic acid

A mixture of 1.6 g (6.2 mmol) of the product from step D and 4.0 g (12.4 mmol) of azidotributylstannane were heated at 60° C. for 44 hours. The mixture was cooled to ambient temperature. Fifty ml of 6N hydrochloric acid was added and the mixture was heated for 1.5 hours at 80° C. and then at 105° C. for 3 hours. The mixture was cooled, extracted thrice with diethyl ether, and the aqueous layer was concentrated under vacuum. The residue was lyophilized and purified by ion exchange chromatography. The purified solid was refluxed in acetone for 1 hr. The solid was washed with acetone and diethyl ether and dried under vacuum at 80° C. to obtain 1.0g of the desired product, $[\alpha]_D = -18.7°$ (c=1, N HCL). m.p. 162–167° C. (foams). $^1H$ NMR($D_2O$): δ3.57(dd, J=13.0, 3.1 Hz, 1H), 3.44 (bd, J=11.1 Hz, 1H), 2.96 (m, 3H), 2.21 (m, 2H), 1.82(d, J=14.2Hz, 1H), 1.40(m, 2H).

EXAMPLE 9 trans-(±)-4-(1(2)H-Tetrazol-5-yl)methyl]-2-piperidinecarboxylic acid

A. Ethyl trans-(±)-4-cyanomethyl-N-vinyloxycarbonyl-2-piperidinecarboxylate

Following the procedure of Example 8(D), 2.1 g (8.7 mmol) of the trans diastereomer of Example 8(A) was reacted with 1.9 g (17.4 mmol) of vinyl chloroformate and 3.7 g (17.4 mmol) of 1,8-bis-dimethylaminonaphthalene to obtain 2.1 g (88%) of the desired intermediate.

B. trans-(±)-4-[(1(2)H-Tetrazol-5-yl)methyl]-2-piperidinecarboxylic acid

Following the process of Example 8(E), 3.4 g (12.7 mmol) of the compound prepared above was reacted with 11.0 g (33.1 mmol) of azidotributylstannane to obtain 1.8 g (68%) of the desired product, m.p. 263-265°.

As noted above, the compounds of this invention are excitatory amino acid antagonists. Therefore, another embodiment of the present invention is a method of blocking one or more excitatory amino acid receptors in mammals which comprises administering to a mammal requiring decreased excitatory amino acid neurotransmission a pharmaceutically effective amount of a compound of the invention.

The term "pharmaceutically effective amount", as used herein, represents an amount of a compound of the invention which is capable of blocking one or more excitatory amino acid receptors. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical daily dose will contain from about 0.01 mg/kg to about 20 mg/kg of the active compound of this invention. Preferred daily doses will be about 0.05 to about 10 mg/kg, ideally about 0.1 to about 5 mg/kg.

A variety of physiologic functions have been shown to be subject to influence by excessive stimulation of excitatory amino acid neurotransmission. As such, the compounds of the present invention are believed to have the ability to treat a variety of disorders in mammals associated with this condition which include neurological disorders such as convulsive disorders for example, epilepsy; stroke; anxiety; cerebral ischaemia; muscular spasms; and neurodegenerative disorders such as Alzheimer's Disease and Huntington's Disease. Therefore, the present invention also provides methods of treating the above disorders at rates set forth above for excitatory amino acid receptors in mammals.

The following experiment was conducted to demonstrate the ability of the compounds of the present invention to inhibit responses due to excitatory amino acid agonists. A typical receptor substance is characterized by N-methyl-D-aspartic acid (NMDA).

Male Charles River CF1 mice held in the laboratory for a minimum of three days were housed, 12 per cage, on sawdust bedding in clear plastic boxes with wire mesh lids. Animals were allowed full access to feed and water prior to testing.

Unless otherwise specified, all test compounds were formulated in dimethylsulfoxide (DMSO) and diluted to a 5% DMSO/sterile water solution by volume. Dosing began at 160 mg/kg. If any significant activity was detected, the test drug dose was divided in half until no more activity was detected. All test compounds were administered using the intraperitoneal injection (i.p.) route at a volume of 0.01 cc/gm.

Five mice were taken from the plastic cages, dosed with the test compound and placed individually in clear plastic observation cages. After a 30 minute drug absorption period, the mice were injected intraperitoneally with 200 mg/kg of NMDA. This dose of NMDA produces death in more than 95% of control-treated animals. Twenty minutes after the NMDA injection the animals were scored as dead or alive. Data are reported as the minimum effective dose (MED) to block NMDA-induced lethality. Protection from lethality is met by the survival of at least three of the five animals. The data is set forth in Table I below. Data for AP5 and AP7, known excitatory amino acid antagonists, are provided for comparison.

TABLE I

| In Vivo NMDA Induced Lethality | |
|---|---|
| Example No. of Compound Tested | MED (mg/kg) |
| 1 | 20 |
| 2 | 10 |
| 3 | 10 |
| 4 | 20 |
| 5 | 160 |
| 7 | 160 |
| 8 | 5 |
| 9 | 80 |
| AP5 | 80 |
| AP7 | 160 |

In another experiment, male or female neonatal (7 to 8 days old) Sprague-Dawley rats were removed from the dam and placed in plastic observation chambers that were maintained at 30-32° C. All test drugs were dissolved in normal saline. Activation of NMDA receptors in these rats leads to a readily observable generalized motor seizure in over 95% of the animals. These seizures are not blocked by administration of a non-NMDA selective antagonist drug, but are readily blocked by NMDA selective compounds.

Animals were injected by the intraperitoneal route with the test drug (1 ml/100 g of body weight) and observed for a 30 minute period for seizure (potential agonist) activity. They were then injected with NMDA at a dose of 20 mg/kg body weight i.p. to test for antagonist activity. Rats were observed for seizures for an additional 30 minutes following NMDA administration. Animals were rated as being positive or negative for the clear demonstration of tonic-clonic seizure activity with loss of righting ability. Generally, five animals were used at each dose of compound. Doses were decreased in a stepwise fashion until at least 3 out of 5 animals exhibited seizures. The minimum effective dose was the lowest test dose which prevented NMDA-induced seizures in at least three out of five animals.

The MED of Example 6 in the above test was 200 mg/kg.

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate microcrystalline cellulose, polyvinylpyrrolidone, cellulose, water syrup, methyl cellulose, methyland propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
|---|---|
| (−)-4-[3-(1(2)H-Tetrazol-5-yl)propyl]-2-piperidinecarboxylic acid | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| cis-(−)-4-[(1(2)H-Tetrazol-5-yl)methyl]-2-piperidinecarboxylic acid | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|  | Weight % |
|---|---|
| (±)-4-[2-(1(2)H-Tetrazol-5-yl)ethyl]-2-piperidinecarboxylic acid | 0.25 |
| ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

|  |  |
|---|---|
| (±)-3-[2-(1(2)H-Tetrazol-5-yl)ethyl]-2-piperidinecarboxylic acid | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

|  |  |
|---|---|
| (±)-3-[3-(1(2)H-Tetrazol-5-yl)propyl]-2-piperidinecarboxylic acid | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

| | |
|---|---|
| (±)-4-[2-(1(2)H-Tetrazol-5-yl)ethyl]-2-piperidinecarboxylic acid | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | |
|---|---|
| (±)-4-[2-(1(2)H-Tetrazol-5-yl)ethyl]-2-piperidinecarboxylic acid | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | |
|---|---|
| (±)-4-[2-(1(2)H-Tetrazol-5-yl)ethyl]-2-piperidinecarboxylic acid | 100 mg |
| isotonic saline | 1000 ml |

The solution of the above ingredients is administered intravenously at a rate of 1 ml per minute to a subject in need of treatment.

I claim:

1. A compound of the formula

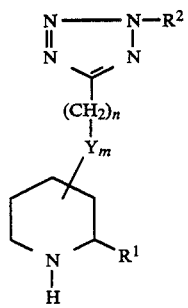

I wherein
the compound is in the (−) form;
$R^1$ is

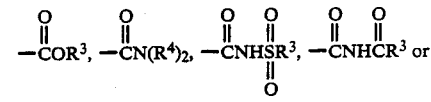

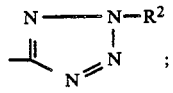

$R^2$ is hydrogen or $C_1$-$C_3$ alkyl;
n is 0, 1, 2 or 3;
m is 0 or 1;
provided that the sum of m and n is 0, 1, 2 or 3;
$R^3$ is hydrogen, $C_1$-$C_4$ alkyl, phenyl or an oral ester forming group;
Y is —CH=;
each $R^4$ is independently hydrogen, $C_1$-$C_4$ alkyl or phenyl; or
a pharmaceutically acceptable salt thereof.

2. A compound of claim 1 wherein $R^1$

3. A compound of claim 2 which is the (−) isomer.
4. A compound of claim 2 wherein $R^3$ is hydrogen.
5. A compound of claim 4 wherein n is 1.
6. The compound of claim 5 which is 4-[(1(2)H-tetrazol-5-yl)methyl]-2-piperidinecarboxylic acid or a diastereomer or stereospecific isomer thereof, or a pharmaceutically acceptable salt thereof.
7. The compound of claim 6 which is cis-(−)-4[(1(2)H-tetrazol-5-yl)methyl]-2-piperidinecarboxylic acid, or a pharmaceutically acceptable salt thereof.
8. A compound of claim 4 wherein n is 2.
9. The compound of claim 8 which is 4-[2-(1(2)H-tetrazol-5-yl)ethyl]-2-piperidinecarboxylic acid or a diastereomer or stereospecific isomer thereof, or a pharmaceutically acceptable salt thereof.
10. A compound of claim 4 wherein n is 3.
11. The compound of claim 10 which is 4-[3-(1(2)H-tetrazol-5-yl)propyl]-2-piperidinecarboxylic acid or a diastereomer or stereospecific isomer thereof, or a pharmaceutically acceptable salt thereof.
12. The compound of claim 1 which is 4-[(1(2)H tetrazol-5-yl)methylidene]-2-piperidinecarboxylic acid or a diastereomer or stereospecific isomer thereof, or a pharmaceutically acceptable salt thereof.
13. A compound of claim 1 wherein the oral ester forming group is $C_1$-$C_4$ alkoxy; benzyloxy; benzyloxy substituted on the phenyl ring with halogen, $C_1$-$C_4$ alkyl or $C_1$-$C_4$ alkoxy; $C_1$-$C_5$ alkanoyloxymethoxy; or $C_1$-$C_5$ alkanoyloxymethoxy substituted on the oxomethyl with $C_1$-$C_4$ alkyl or $C_4$-$C_7$ cycloalkyl.
14. A method of blocking one or more excitatory amino acid receptors in mammals which comprises administering to a mammal requiring decreased excitatory amino acid neurotransmission a pharmaceutically effective amount of a compound of claim 1.
15. A method of treating epilepsy in mammals comprising administering to the mammal in need of treatment from epilepsy an antiepileptic amount of a compound of claim 1.
16. A method of treating stroke in mammals comprising administration to a mammal requiring treatment from a stroke an antistroke amount of a compound of claim 1.

17. A method of treating anxiety in mammals comprising administration to a mammal requiring treatment from anxiety an antianxiety amount of a compound of claim 1.

18. A method of treating cerebral ischaemia in mammals comprising administration to a mammal requiring treatment from cerebral ischaemia an antiischaemic amount of a compound of claim 1.

19. A method of treating muscular spasms in mammals comprising administration to a mammal requiring treatment from muscular spasms an antispasmodic amount of a compound of claim 1.

20. A method of treating Alzheimer's Disease in mammals comprising administration to a mammal requiring treatment from Alzheimer's Disease a pharmaceutically effective amount of a compound of claim 1.

21. A method of treating Huntington's Disease in mammals comprising administration to a mammal requiring treatment from Huntington's Disease a pharmaceutically effective amount of a compound of claim 1.

22. A pharmaceutical formulation for the treatment of neurological disorders comprising a pharmaceutically effective amount of a compound of claim 1 and a pharmaceutically acceptable carrier, diluent or excipient therefor.

* * * * *